United States Patent [19]

Anderson et al.

[11] Patent Number: 5,798,331

[45] Date of Patent: Aug. 25, 1998

[54] SUCCINIC ACID DERIVATIVES AND THEIR USE AS SURFACTANTS

[75] Inventors: Steven John Anderson; Neil Michael Carpenter, both of Cleveland, United Kingdom

[73] Assignee: Imperial Chemical Industries PLC, London, England

[21] Appl. No.: 849,099

[22] PCT Filed: Nov. 29, 1995

[86] PCT No.: PCT/GB95/02785

§ 371 Date: May 28, 1997

§ 102(e) Date: May 28, 1997

[87] PCT Pub. No.: WO96/16930

PCT Pub. Date: Jun. 6, 1996

[30] Foreign Application Priority Data

Dec. 2, 1994 [GB] United Kingdom .................. 9424353

[51] Int. Cl.$^6$ ...................................................... C11D 1/66
[52] U.S. Cl. ................................................ 510/501; 544/36
[58] Field of Search ...................... 510/501; 544/162, 544/404; 546/245; 548/568; 554/36; 514/237.5, 255, 315, 423; 106/505

[56] References Cited

U.S. PATENT DOCUMENTS

| | | |
|---|---|---|
| 3,707,511 | 12/1972 | Vincent et al. . |
| 3,991,056 | 11/1976 | Okamoto et al. .............. 260/268 C |
| 5,559,232 | 9/1996 | Ackermann et al. .............. 544/121 |
| 5,620,952 | 4/1997 | Fu et al. .............. 510/350 |

FOREIGN PATENT DOCUMENTS

| | | |
|---|---|---|
| 0 584 711 | 3/1994 | European Pat. Off. . |
| 05/125014 | 5/1993 | Japan . |
| 94 00508 | 1/1994 | WIPO . |

OTHER PUBLICATIONS

Chemical Abstracts, vol. 119, No. 17, Oct. 25, 1993, Columbus, Ohio, US: Abstract No. 180393, Fujio A. et al. 'Preparation of alkyl–or alkenylsuccinic acid ester derivatives as surfactants with low irritability' see abstract & JP.A.93 125 014 (Kao Corp; Japan) May 21, 1993.

*Primary Examiner*—Douglas J. McGinty
*Assistant Examiner*—John R. Hardee

[57] ABSTRACT

Compounds of formula (I), where $R^1$, $R^2$, $R^3$, $R^4$ and $R^5$ have defined meanings

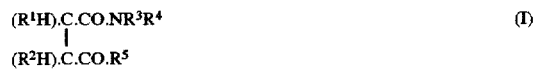

are useful as surfactants especially in agrochemical formulations, pigment dispersions and domestic detergent formulations. Compounds where one of $R^1$ and $R^2$ is hydrogen and the other is $C_8$ to $C_{18}$ straight chain alkenyl group, the group —$NR^3R^4$ is the residue of a glycamine, especially a glucamine, and $R^5$ is —$NR^3R^4$ as defined (especially a glycamine residue) or a group $O.(AO)_n.R^6$ where AO is an alkylene oxide, especially an ethylene oxide, residue, n is especially from 3 to 50 and $R^6$ is a $C_1$ to $C_6$ alkyl group, are particularly desirable.

22 Claims, No Drawings

SUCCINIC ACID DERIVATIVES AND THEIR USE AS SURFACTANTS

This invention relates to surfactants and in particular to novel surfactants based on derivatives of substituted succinic acids and to the use of these surfactants particularly as adjuvants in agrochemical formulations and as dispersants and/or emulsifiers in agrochemical, as dispersants for pigments, especially in aqueous dispersions, as emulsifiers in emulsion polymerisation, as surfactants in domestic detergents, particularly heavy duty laundry liquids, especially non-aqueous heavy duty laundry liquids, and other applications.

In recent years there has been an increasing desire to replace well established surfactants with materials of increased biodegradability. There is, however, great practical difficulty in devising alternatives to substances of excellent performance which have maintained an important position in the market for several decades.

EP 0107199 B and published PCT Application No WO 94/00508 A describe surfactants based on alk(en)yl substituted succinic acid alkylene oxide esters and amides.

This invention is based on the discovery of substituted di-amides or amide esters of alkenyl succinic acids, particularly where the amide group is a glucamide group. These compounds have particular utility as surfactants and/or adjuvants in agrochemical formulations; as dispersants for pigments e.g. in aqueous dispersions of pigments, especially $TiO_2$, particularly for use in paints; and as surfactants in laundry formulations, especially heavy duty laundry formulations.

This invention accordingly provides compounds of the formula (I):

$$(R^1H).C.CO.NR^3R^4 \atop | \atop (R^2H).C.CO.R^5 \qquad (I)$$

where
one of $R^1$ and $R^2$ in the succinic acid moiety is $C_6$ to $C_{22}$ alkenyl or alkyl and the other is hydrogen;
$R^3$ is a polyhydroxy hydrocarbyl radical;
$R^4$ is hydrogen, $C_1$ to $C_{22}$ hydrocarbyl, particularly $C_1$ to $C_{20}$ alkyl, $C_7$ to $C_{12}$ aralkyl, $C_2$ to $C_{20}$ hydroxyl substituted alkyl e.g. ethanoyl (2-hydroxyethyl), or $R^4$ is independently as defined above for $R^3$;
$R^5$ is a group: —$NR^3R^4$ where $R^3$ and $R^4$ are independently as defined above; or
$R^5$ is a group: —$O.(AO)_n.R^6$ where:
AO is an alkylene oxide, particularly an ethylene oxide, residue;
n is 1 to 200, preferably 2 to 100 (and as it is an average it may be non-integral); and
$R^6$ is hydrogen, $C_1$ to $C_{22}$ hydrocarbyl, particularly $C_1$ to $C_{20}$ alkyl, especially $C_1$ to $C_6$ alkyl such as methyl, ethyl, propyl or butyl; or
$R^6$ is a group:

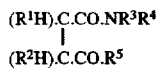

where $R^1$, $R^2$, $R^3$ and $R^4$ are independently as defined above; or
$R^6$ is a group: —$NR^7R^8$ where:
$R^7$ is hydrogen, $C_1$ to $C_{22}$ hydrocarbyl, particularly $C_1$ to $C_{20}$ alkyl, especially $C_1$ to $C_6$ alkyl such as methyl, ethyl, propyl or butyl;

$R^8$ is $C_1$ to $C_{22}$ hydrocarbyl, particularly $C_1$ to $C_{20}$ alkyl, especially $C_1$ to $C_6$ alkyl such as methyl, ethyl, propyl or butyl; or
—$NR^7R^8$ is a pyrrolidino-, piperidino-, morpholino-, piperazino, or a N—($C_1$ to $C_6$ alkyl) piperazino-group; or
—$NR^7R^8$ is a group of the formula —$NH.(AO)n.R^9$ where AO and n are as defined above and $R^9$ is a $C_1$ to $C_{22}$ hydrocarbyl group, particularly an alkyl group; or
—$NR^7R^8$ is a group of the formula —$NH.(AO)_p.CH_2CH_2.OR^{10}$
where AO is as defined above;
p is from 0 to 200, particularly 0 to 100; and
$R^{10}$ is a $C_1$ to $C_{22}$ hydrocarbyl, particularly $C_1$ to $C_{20}$ alkyl, especially $C_1$ to $C_6$ alkyl such as methyl, ethyl, propyl or butyl; or
$R^{10}$ is a group:

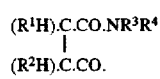

where $R^1$, $R^2$, $R^3$ and $R^4$ are independently as defined above.

The following particular sub-groups of compounds of the formula (I) form specific aspects of the invention:

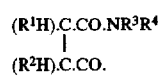   (Ia)

where $R^1$, $R^2$, $R^3$ and $R^4$ are independently as defined above and the respective groups —$NR^3R^4$ are desirably, but not necessarily, the same.

   (Ib)

where $R^1$, $R^2$, $R^3$, $R^4$, AO, n and $R^6$ are as defined above.

   (Ic)

where $R^1$, $R^2$, $NR^3R^4$, AO and n are as defined above and the respective groups $R^1/R^2$ and —$NR^3R^4$ are desirably, but not necessarily, the same.

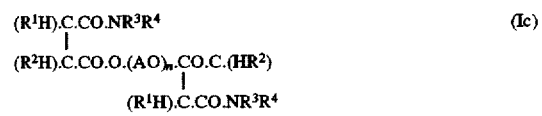   (Id)

where $R^1$, $R^2$, $R^3$, $R^4$, AO, n and $R^9$ are as defined above.

   (Ie)

where $R^1$, $R^2$, $R^3$, $R^4$, AO and p are as defined above and the respective groups $R^1/R^2$ and —$NR^3R^4$ are desirably, but not necessarily, the same.

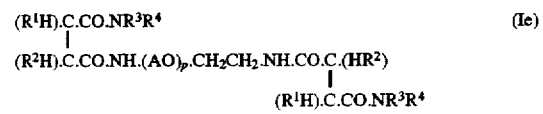   (If)

where $R^1$, $R^2$, $R^3$, $R^4$, $R^7$ and $R^8$ are as defined above.

Among the compounds of the invention, those where the alk(en)yl group $R^1/R^2$ is a $C_8$ to $C_{18}$ alkenyl or alkyl group are especially desirable. Similarly, compounds where the group $R^1$ or $R^2$ is an alkenyl group are more desirable than those where the group is alkyl. Compounds where the group $R^1$ or $R^2$ is an alkenyl group, particularly a $C_8$ to $C_{18}$ alkenyl group form a specific aspect of the invention. It is desirable that the $R^1/R^2$ alkyl or alkenyl group(s) of the compounds of the invention have straight chains. Where the chain is not straight it is desirable that it has at most a total of two and preferably only one branch(es) on average. Preferably the whole molecule comprises at most three branches in total in all alkyl and alkenyl groups present.

The group $R^3$ is a polyhydroxy hydrocarbyl radical, particularly one having a linear carbon chain of from 4 to 7 carbon atoms and at least three hydroxyl groups directly bonded to chain carbon atoms. The group may include substituents, in particular, alkoxy groups e.g. by etherification of further hydroxyl groups or polyalkylene oxide chains, but the group desirably includes at least three free hydroxyl groups including such hydroxyl groups on substituents of the basic chain. Particularly $R^3$ is an open chain tetratol, pentitol, hexitol or heptitol group or an anhydro derivative of such a group. Especially desirably, $R^3$ is the residue of, or a residue derived from, a reducing sugar, particularly a monosaccharide such as glucose or fructose, a disaccharide such as maltose or palitose or a higher oligosaccharide. Where $R^3$ is the residue of, or a residue derived from, a monosaccharide, the saccharide derived group or residue will usually be present as an open chain material. In the compounds of this invention the group $R^3$ is present as or as part of the hydrophile. Thus it will usually be desirable that the hydrophilicity of this group is not unduly reduced. The open chain form of such groups is typically the most hydrophilic form and will thus usually be the form desired. Groups including internal cyclic ether functionality can however be used, if desired, and may be obtained inadvertently if the synthetic route exposes the group to relatively high temperatures or other conditions which promote etherification.

Where $R^3$ is the residue of, or a residue derived from, an oligosaccharide it can be considered as an open chain mono-saccharide derived group or residue with a saccharide or oligosaccharide substituent. Particularly useful $R^3$ groups are derived from glycoses and are of the formula: $-CH_2.(CHOH)_4 CH_2OH$, e.g. corresponding to residues from glucose, mannose or galactose. In this case the group $-NR^3R^4$ is of the formula: $-NR^4.CH_2.(CHOH)_4 CH_2OH$ and the group is conveniently called a glycamine group and the corresponding amides can be called glycamides. Most commonly the group $R^3$ will be derived from glucose and the corresponding amine and amides are called glucamines and glucamides.

$R^4$ can be hydrogen, hydrocarbyl or independently a group as defined for $R^3$. When $R^4$ is hydrocarbyl, is will usually either be a short chain e.g. a $C_1$ to $C_6$, alkyl group, particularly a methyl, ethyl, propyl or butyl group, or a hydroxyalkyl group such as an ethanoyl (2-hydroxyethyl) group. Alternatively, it can be a longer chain group which can act as a further hydrophobe such as a $C_8$ to $C_{18}$ alkyl or $C_7$ to $C_{12}$ aralkyl group. When $R^4$ is a group as defined for $R^3$, it can act as a further hydrophile. These possibilities open up opportunities for tailoring the relative hydrophilicity or hydrophobicity of the molecule to suit specific end uses.

The group $-NR^3R^4$ can be regarded as the residue of the amine $H.NR^3R^4$ [this amine is used in typical syntheses of compounds of the formula (I)—see below]. Amines of the formula $H.NR^3R^4$ where $R^4$ is a sugar residue, can conveniently be made from reducing sugars by a reductive amination reaction, followed, if necessary, by alkylation (or reductive alkylation) to substitute the group $R^4$ in the primary amine $H_2NR^4$.

The alkylene oxide group AO is typically a group of the formula: $-(C_mH_{2m}O)-$ where m is typically 2, 3 or 4, desirably 2 or 3, i.e. an ethylene oxide or propylene oxide group, and it may represent different groups down the alkylene oxide chain. Generally, it is desirable that the chain is a homopolymeric ethylene oxide chain. However, the chain may be a homopolymer chain of propylene glycol residues or a block or random copolymer chain containing both ethylene glycol and propylene glycol residues.

The chain length of the polyalkylene oxide group, when present, i.e. the value of the parameter n or p, will generally be chosen to provide the desired properties in the intended product. Typically, where the polyalkylene oxide chain is a polyethylene glycol chain it will usually have 1 to 100, more usually 3 to 50, corresponding very approximately to chains derived from PEG 50 to PEG 2000, ethylene glycol residues and where it is a polyoxypropylene chain it will usually have 1 to 50 propylene glycol residues. Where the chain is a block or random copolymer of ethylene and propylene glycol residues the chain length chosen will typically correspond to the above ranges but numerically according to the proportion of ethylene and propylene glycol residues in the chain. Of course, numerical values of numbers of repeat units in the polyoxyalkylene chain are average values. As is common to surfactants containing a polyoxyalkylene chain, the higher the proportion of ethylene glycol residues, and the longer the polyethylene glycol chain, and the more hydrophilic the product.

When, in formula (I), $R^6$ is H or hydrocarbyl, particularly alkyl, if $R^6$ is H, the products tend to be relatively more hydrophilic and if it is a hydrocarbyl, particularly alkyl group, relatively less hydrophilic. Where $R^6$ is a relatively long chain group e.g. a $C_8$+alkyl group, then this group will tend to act as a second hydrophobe. The group $R^6$ will be chosen according to the desired overall properties of the compound in the intended end use application.

The compounds of the invention can be made by reacting a reactive precursor, typically an ester of a corresponding substituted succinic acid with an alcohol of the formula $R^{11}OH$ (as defined below), with an amine of the formula $H.NR^3R^4$, where $R^3$ and $R^4$ are as defined above, in a molar ratio corresponding to the number of amide functions in the final product and removing the alcohol $R^{11}OH$ generated, typically by distillation. As applied to compounds of the formulae (Ia) to (If) specific syntheses are outlined below.

Compounds of the invention of the formula (Ia) can be made by reacting one mole of a diester:

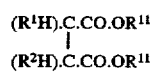

where $R^1$ and $R^2$ are as defined above for formula (Ia) and $R^{11}$ is a lower alkyl group, particularly a $C_1$ to $C_4$ alkyl, e.g. an ethyl, butyl or, and especially, a methyl group, with two moles of amine: $H.NR^3R^4$ where $R^3$ and $R^4$ are as defined above for formula (Ia).

The diester intermediate can be made by esterifying a corresponding alk(en)yl succinic anhydride with an alcohol $R^{11}OH$ (where $R^{11}$ is as defined above), especially methanol. The esterification can conveniently be carried out by one of two methods:

i Alcohol $R^{11}OH$ is added to the anhydride and the mixture stirred typically for between 20 minutes and 2 hours typically at moderately elevated temperatures e.g. from 40° to 120° C. A catalytic amount of acid such as sulphuric acid, is then added and the mixture heated, typically to a reaction mix temperature of from 80° to 150° C., particularly 100° to 120° C. where the alcohol is methanol, and alcohol and water, from the esterification reaction, removed by distillation. Fresh alcohol is gradually added to maintain the volume of the reaction mix and to drive the reaction to completion. Typically, the reaction is complete in from 1 to 3 hours. The usually liquid di-ester product can be recovered by distilling off excess alcohol, cooling the reaction mix, neutralising the acid catalyst e.g. with sodium hydrogen carbonate, and removing insoluble salts by filtration.

ii Alcohol $R^{11}OH$ is added to the anhydride along with a catalytic amount of acid such as sulphuric acid. The reaction mix is then heated typically to a reaction mix temperature of from 80 to 150° C., particularly 100° to 120° C. where the alcohol is methanol, and alcohol and water, from the esterification reaction, are removed by distillation. Fresh alcohol is gradually added to maintain the volume of the reaction mix and to drive the reaction to completion. Typically, the reaction is complete in from 1 to 3 hours. The usually liquid di-ester product can be recovered by distilling off excess alcohol, cooling the reaction mix, neutralising the acid catalyst e.g. with sodium hydrogen carbonate, and removing insoluble salts by filtration.

Compounds of the formula (Ib) can be made by:

i reacting one mole of a compound:

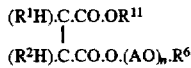

where $R^1$, $R^2$, AO, n and $R^6$ are as defined above for formula (Ib), and $R^{11}$ is as defined above, with one mole of amine: $H.NR^3R^4$ where $R^3$ and $R^4$ are as defined above for formula (Ib); or ii reacting one mole of a compound:

where $R^1$, $R^2$, $R^3$, $R_4$ are as defined above for formula (Ib), and $R^{11}$ is as defined above, with one mole of an alkylene oxide or derivative: $HO.(AO)_n.R^6$ where AO, n and $R^6$ are as defined above for formula (Ib).

In sequence i, the alkyl/(polyalkylene oxide) bis-ester intermediate can be made by reacting one mole of corresponding alk(en)yl succinic anhydride with one mole of corresponding polyalkylene oxide (which may be mono-end capped) to form a mono-(polyalkylene oxide) ester followed by esterification with excess alcohol $R^{11}OH$. In sequence ii, the amide/ester starting material can be made by reacting one mole of corresponding alk(en)yl succinic acid di-$R^{11}$ ester with one mole of amine $H.NR^3R^4$. Sequence i is preferred because it minimises the possibility of forming a diamide or amide amine salt of the diacid during the preparation of the intermediate.

Compounds of the formula (Ic) can be made by reacting one mole of a compound:

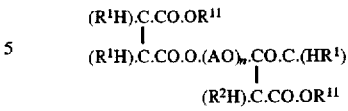

where $R^1$, $R^2$, AO and n are as defined above for formula (Ic), and $R^{11}$ is as defined above, with two moles of amine: $H.NR^3R^4$ where $R^3$ and $R^4$ are as defined above for formula (Ic). The polyalkylene oxide bis(succinic acid ester) intermediate can be made by reacting one mole of corresponding dihydroxy-polyalkylene oxide (polyoxyalkylene glycol) with two moles of corresponding alk(en)yl succinic anhydride followed by esterification with excess alcohol $R^{11}OH$.

Compounds of the formula (Id) can be made by reacting one mole of a compound:

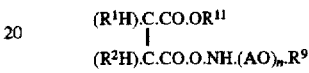

where $R^1$, $R^2$, AO, n, and $R^9$ are as defined above for formula (Id) and $R^{11}$ is as defined above, with one mole of amine: $H.NR^3R^4$ where $R^3$ and $R^4$ are as defined above for formula (Id). The ester/amide starting material can be made by reacting one mole of corresponding alk(en)yl succinic acid di-$R^{11}$ ester with one mole of amine: $NH_2.(AO)_n.R^9$ where AO, n and $R^9$ are as defined above.

Compounds of the formula (Ie) can be made by reacting one mole of a compound:

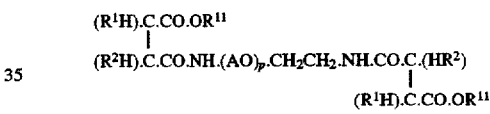

where $R^1$, $R^2$, AO and p are as defined above for formula (Ie) and $R^{11}$ is as defined above, with two motes of amine: $H.NR^3R^4$ where $R^3$ and $R^4$ are as defined above for formula (Ie). The intermediate polyoxyalkylene diamine bis-amide/ diester can be made by reacting one mole of amine: $NH_2.(AO)_p.CH_2CH_2.NH_2$ with two moles of corresponding alk (en)yl succinic acid di-$R^{11}$ ester.

Compounds of the formula (If) can be made by reacting one mole of a compound:

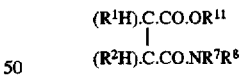

where $R^1$, $R^2$, $R^7$ and $R^8$ are as defined above for formula (If), and $R^{11}$ is as defined above, with amine: $H.NR^3R^4$ where $R^3$ and $R^4$ are as defined above for formula (If). The intermediate ester/amide can be made by reacting one mole of corresponding alk(en)yl succinic acid di-$R^{11}$ ester with one mole of amine: $H.NR^7R^8$.

Typically, in the amidation reactions the amide reaction product is favoured so that the alcohol $R^{11}OH$ by-product does not generally need to be removed to drive the reaction towards completion. However, the alcohol will usually be removed e.g. by distillation, to purify the desired diamide product. Generally the amidation reactions proceed under relatively mild conditions e.g. by heating to a temperature of from 50° to 150° C., particularly from 90° to 130° C., either neat or in solution in a suitable solvent or diluent such as monopropylene glycol or a suitably liquid polyethylene glycol (PEG) such as PEG 200. We have not found it necessary to use a catalyst for this reaction, but catalysts usefully speed the reaction. Suitable catalysts include alkoxides, particularly alkali metal alkoxides such as sodium methoxide, and transition metal compounds such as tertiary butyl titanate (TBT) and zirconium butoxide.

Reactions between a precursor anhydride and hydroxylic reagents such as an alcohol, polyalkylene glycol or mono-end capped polyalkylene glycol can readily be carried out, with or without catalysts, by bringing the hydroxylic reagent into contact with the alk(en)yl succinic anhydride. Reaction occurs typically at temperatures below 200° C. and even below 100° C. The reactants will usually be used in at least approximately stoichiometric proportions. Particularly where stoichiometric proportions are used, further purification does not usually appear to be necessary, but can be carried out if desired.

Reactions of mono carboxylic acid intermediates with alcohol $R^{11}OH$ (typically used in molar excess) to generate lower alkyl ester intermediates can be carried out in a conventional manner for example using an acid catalyst which may be sulphuric, toluene sulphonic or a phosphoric acid. Phosphoric acids can be particularly useful as, after neutralisation, they may be a useful component of detergent compositions which include the surfactants of this invention.

The products of the invention are typically a mixture of isomers corresponding to the two senses of anhydride ring opening during synthesis. We have noted that the alkenyl or alkyl chain seems to have a minor steric effect on the isomer ratio with the isomer ratio being typically about 60:40, the major isomer arising from nucleophilic attack at the anhydride carbonyl group remote from the alkenyl or alkyl group (probably because of steric hindrance). The alkenyl succinic anhydride precursors may be produced by reacting maleic anhydride with an olefin having 6 to 22, particularly 8 to 18, carbon atoms, preferably with an excess, for example a 50 to 200% excess, of olefin at a temperature in the range 150° to 400° C. and preferably 180° to 250° C. and removing excess olefin for example by distillation which is suitably carried out under vacuum. No catalyst is necessary, but it is preferred than an antioxidant is present. These anhydrides are well known commercial materials. In alkenyl succinic anhydrides prepared as described above the double bond normally lies in the 2-position in the alkenyl substituent.

To make products where the group $R^1$ or $R^2$ is an alkyl group then either the unsaturated products can be hydrogenated or, and preferably, the intermediate alkenyl succinic anhydride can be hydrogenated to give an alkyl succinic anhydride. Typically, hydrogenation of the anhydride is carried out over a hydrogenation catalyst such as Raney nickel or a Pd/C catalyst. Temperatures of from 15° to 100° C. and pressures of up to 200 bar absolute may be used and, if desired a solvent may be present. For example, the hydrogenation reaction on an alkenyl succinic anhydride may be carried out at 20° C. at 1 bar $H_2$ pressure using 5% w/w of Pd/C catalyst over a period of for example 6 to 24 hours.

Compounds according to the invention have emulsification properties and wetting and dispersion capabilities. These properties make the compounds of the invention suitable for use as surfactants in agrochemical formulations. In addition, in agrochemical formulations they can act as adjuvants for example with herbicides such as glyphosate and sulfosate, fungicides such as Iprodione, Carbendazym and Propionazole, insecticides, acaricides and plant growth regulator formulations. The invention accordingly includes agrochemical formulations including, in addition to at least one agrochemically active component, at least one compound of the invention as surfactants and/or adjuvants; and the invention further includes the use of the compounds of this invention as surfactants and/or adjuvants in agrochemical formulations. Generally, when used in agrochemical formulations, the compounds of this invention will typically be used at a concentration of 1 to 30% based on the formulation when used as surfactants e.g. to disperse the agrochemical(s) and when used as adjuvants, they will typically be used in a concentration of from 5 to 60% based on concentrate formulations and 1 to 100% in or as components for addition to tankmixes. Other conventional components can be included in such formulations such as one or more of oils e.g. mineral oil(s), vegetable oil(s) and alkylated vegetable oil(s) which are, typically $C_1$ to $C_8$, alkyl mono esters of vegetable oil fatty acids: solvents and/or diluents such as ethylene and/or propylene glycol or low molecular weight alcohols, which act to solublise the formulation and/or to reduce the viscosity and/or to avoid or reduce dilution problems e.g. the formation of gels; and other surfactants which may be anionic surfactants, cationic surfactants or non-ionic surfactants such as alcohol alkoxylates, usually ethoxylates, or alkyl phenol alkoxylates, usually ethoxylates. Such other components will, as with formulations using purely conventional surfactants, be used in amounts based on the desired effect.

The properties of the surfactants of this invention also make them suitable as dispersants for pigments, including inorganic pigments such as titanium dioxide, pigmentary iron oxide ($Fe_2O_3$) and organic pigments such as phthalocyanine blue and green pigments and carbon black, and similar materials. The present surfactants are particularly useful in aqueous dispersions of titanium dioxide pigments especially for ultimate use in paints. Accordingly, the invention includes the use of at least one compound of this invention as dispersant(s) for pigments in dispersions, especially aqueous dispersions, particularly of titanium dioxide; and the invention further includes dispersions of pigments, especially aqueous dispersions, particularly of titanium dioxide, including compounds of this invention as dispersants. The amount of surfactant used in such dispersant applications depends on the materials employed and the concentration of dispersion required, but will usually be in the range 0.2 to 10% by weight of the pigment. In aqueous dispersions, for inorganic pigments such as titanium dioxide and iron oxide pigment the amount used is typically in the range 0.05 to 5%, more usually 0.1 to 2.5%, by weight of the solid dispersed and for organic pigments such as phthalocyanine pigments and carbon black typically the amount used is in the range 3 to 10% by weight of the solid dispersed. Typical dispersions made using the surfactants of the invention as dispersants can contain up to about 70%, often up to about 65%, of inorganic pigment and up to about 35% by weight organic pigment, but this may be up to 50% for pigment pastes. When incorporated into end use products such as paints typical pigment levels on the final product will be about 3 to about 30%, particularly about 20 to about 25%, for inorganic pigments, about 1 to about 15% for organic pigments, particularly about 10 to about 12%, especially for phthalocyanine type organic pigments, and about 0.5 to about 5%, particularly about 3 to about 3%, for carbon black. The continuous phase in such dispersions will usually be water, but the surfactants of this invention can also be used in dispersing solids, particularly pigments such as those described above, in non-aqueous media such as white spirit or aromatic media. The invention further includes a paint including a pigment dispersion as described above.

The surfactants also find use in domestic detergents and the invention accordingly includes the use of the compounds of this invention as surfactants in domestic detergents, particularly in heavy duty laundry powders and liquids, in particular substantially non-aqueous heavy duty laundry liquids; and the invention further includes domestic detergents, particularly in heavy duty laundry powders and liquids, in particular substantially non-aqueous heavy duty laundry liquids, including at least one compound of this invention as surfactants. In laundry applications the surfactants of this invention may be used as the only surfactant or in combination with one or more other, non-ionic, anionic and/or cationic surfactants. Formulations including surfactants of this invention for laundry use will typically also include further components including one or more of builders; corrosion inhibitors such as sodium silicate or disilicate; anti-redeposition aids such as carboxy methyl cellulose; and optical brighteners. Commonly used further components include perfumes; enzymes, including lipases, proteases, cellulases and/or amylases; bleaches, typically based on sodium perborate, sodium percarbonate or similar materials, which will typically be used with bleach activators such as tetra-acetyl ethylene diamine (TAED); and stabilisers such as phosphonates or ethylene diamine tetra-acetic acid (EDTA) usually as the sodium salt; soaps; foam control agents (soaps are often used for this purpose) and fabric conditioners (softeners) such as quaternary ammonium salts and amine oxides which may be coated onto bentonite type clays.

Builders typically used in laundry formulations include phosphate based builders, particularly sodium tripolyphosphate; organic builders such as citrate and/or tartrate; and/or zeolite builders. Powder formulations will often include flow and/or filter aids and may include co-builders such as sodium carbonate and/or bicarbonate, particularly in powders where the builder is a zeolite. However, because the materials typically used as co-builders are alkali, these will not usually be used in formulations intended for hand washing.

Liquid laundry detergent systems are of two broad types, non-aqueous liquids and aqueous liquids. Non-aqueous liquids include a non-aqueous diluent or carrier such as a liquid polyethylene glycol (PEG) such as PEG 150 to 400. The surfactant materials are dispersed in the diluent or carrier usually as miscible liquid phase materials and solid materials, usually mainly builder; co-builder, when used; bleach, when used; and anticorrosion aids are dispersed typically as finely divided solid materials in the diluent or carrier. As is described in our earlier specifications Nos EP 0120569 B and EP 0030096 B such laundry liquids can be made as stable suspensions.

Aqueous liquid laundry liquids can be sub-divided into two types: built liquids, where a solid builder is suspended in a detergent which uses significant amounts of water as the diluent or carrier; and non-built liquids in which the bulk of the product is liquid detergent material. Such aqueous systems, especially the built aqueous systems, cannot readily have their cleaning power increased by the inclusion of simple solid bleaches as they tend to be unstable in the presence of water and the protection of bleaches from decomposition in the presence of free water is at present complex and relatively expensive.

Co-builders such as sodium carbonate and/or bicarbonate are also sometimes used with builders in aqueous built and built non-aqueous system. There is a recent tendency to include relatively small amounts of builders, usually organic builders such as citrate or tartrate in aqueous "unbuilt" formulations. Although such liquids can include alkali co-builders they are not usually used.

Typical composition ranges for heavy duty laundry products of these types is set out in the table below:

| Material | Powder | | Liquid | | | | | |
|---|---|---|---|---|---|---|---|---|
| | | | Aqueous | | | | | |
| | | | built | | unbuilt | | non-aqueous | |
| Surfactant total[1] | 10–30 | (12–20) | 5–35 | (8–30) | 20–60 | (25–45) | 2–30 | (5–20) |
| non-ionic | 1–20 | (5–10) | 1–10 | (2–10) | 5–20 | (8–15) | 2–20 | (5–15) |
| anionic | 0–15 | (3–10) | 0–20 | (5–10) | 5–20 | (8–15) | 0–5 | |
| soap | 0–4 | (1–2) | 0–4 | (1–2) | 0–15 | (8–15) | 0–5 | |
| Builder total[2] | 20–60 | (25–40) | 15–35 | (20–25) | 0–15 | (<10) | 20–50 | (25–45) |
| co-builder | 0–15 | (2–8) | 0–20 | (3–17) | 0–10 | (<5) | 0–10 | (1–5) |
| anti-corrosion aid | 0–15 | (2–5) | 0–15 | (2–5) | 0–4 | | 0–15 | (1–5) |
| Liquid Medium | | | | | | | | |
| water[3] | 0–10 | (2–5) | 30–70 | (30–60) | 20–60 | (20–50) | >5 | (>2) |
| non-aqueous | n/a | | 0–10 | (1–3) | — | — | 20–60 | (30–50) |
| Bleach total[4] | 0–35 | (10–30) | n/a | | n/a | | 0–20 | (5–15) |

(preferred ranges bracketed)
[1]total surfactant includes the surfactant of this invention within the non-ionic part and soap included in powders and aqueous built systems mainly as antifoam,
[2]total builder includes co-builder, anti-corrosion aids and anti-redeposition aids,
[3]water excluding water of crystallisation,
[4]bleach is optional in all formulation types - total bleach includes bleach, bleach activator and bleach stabiliser.

The following Examples illustrate the invention including the manufacture and properties of the compounds of the invention and their end uses, particularly illustrating the versatility and utility of the compounds of the invention. All parts and percentages are by weight unless otherwise specified.

Materials

| Materials | |
|---|---|
| MPG | mono-propylene glycol |
| glyphosate | N-phosphonomethyl glycine as the isopropylamine salt |
| sulfosate | N-phosphonomethyl glycine as the trimethylsulphonium salt |
| ETA | ethoxylated tallow amine formulation adjuvant conventionally used with glyphosate |
| AL 2042 | commercially available alkyl polysaccharide adjuvant conventionally used with sulfosate available from ICI |

Compound Property Test Methods

For products made neat (Synthesis Examples SE1 to SE6 and SE11) the materials tested were the neat materials obtained from the synthesis; for products made using solvents/diluents, (Synthesis Examples SE7 to SE9) the materials tested were the materials obtained from the synthesis which included about 30% reaction solvent/diluent.

| | |
|---|---|
| Surface Tension (ST) | was measured on a 0.1% w/w aqueous solution by the drop method at 23° C.; results are in mN.m$^{-1}$ (1 mN.m$^{-1}$ = 1 dyne.cm$^{-1}$). |
| Cloud Point (CP) | was measured by ASTM D 2024 - 65; results are in °C. |
| Wetting (Wtg) | Draves wetting was assessed using the skein test (ASTM D 2281 - 68); results are in seconds (s) [or minutes (m) - for slow wetters]. |
| Foam height (FH) | Ross Miles foam height was assessed by ASTM D 1173-53 at 25° C.; results are in mm. |

SE1—Dodecenylsuccinic acid bis(N-methyl glucamide)
Dodecenylsuccinic acid dimethyl ester Methanol (50 g; 1.56 mol) was added to dodecenyl succinic anhydride (200 g; 0.75 mol) and the reaction mixture was then heated to reflux and stirred for 1 hour at a reaction mix temperature of about 100° C. with methanol refluxing. A catalytic amount of Sulphuric acid (98% w/v; 0.5 ml) was then added; methanol/water mixture removed by distillation and fresh methanol added to maintain the volume of the reaction mixture. After about 2 hours ca. 500 ml methanol had been added and completion of the reaction was confirmed by the absence of any significant annydride or acid peak in the IR spectrum of a sample of the reaction mix. The excess methanol was distilled off, the reaction mix allowed to cool to ambient temperature, neutralised with sodium hydrogen carbonate and residual solids removed by filtration. The liquid dimethyl ester product was obtained in substantially quantitative yield. The H$^1$ NMR spectrum of the ester product (without further purification) showed 6 methyl ester protons per molecule and C$^{13}$ NMR spectrum showed the absence of anhydride or acid functionality.
Dodecenylsuccinic acid bis(N-methyl glucamide)

N-methyl glucamine (119 g, 0.6 mol) was added to neat dodecenyl succinic acid dimethyl ester (100 g, 0.3 mol), the mixture was then heated to 120° C. and stirred under vacuum at that temperature for 4 hours after which time the IR spectrum of a sample of the reaction mix showed that no ester groups remained (ester band 1740 cm$^{-1}$) and that significant amide product had been made (amide band 1618 cm$^{-1}$). Following the reaction by the IR spectrum showed a steady diminution of the ester band as the amide band strengthened. Similarly, following the reaction by both C$^{13}$ and H$^1$ NMR showed a reduction in intensity of the CH$_3$ ester and the NCH$_3$ amine peaks as the NCH$_3$ amide peak appeared and increased during the reaction. The reaction mix was allowed to cool to ambient temperature to give the bis-glucamide product as a glassy solid in quantitative yield. The identity of the product was confirmed by C$^{13}$ and H$^1$ NMR.

The properties of compound SE1 are as follows:

| Property | Value | Units |
|---|---|---|
| Surface Tension | 39.9 | mN.m$^{-1}$ |
| Cloud Point | >98 | °C. |

-continued

| Property | Value | Units |
|---|---|---|
| Draves Wetting | 68 | seconds |
| Ross Miles Foam Heights | 0 min | 5 min |
| (@60° C.) | 99 | 81 mm |

SE2–SE6 Octenyl to Octadecenyl succinic acid bis(N-methyl glucamide)

The title compounds were made by the method described in Synthesis Example SE1, but substituting the corresponding alkenylsuccinic anhydride for the dodecenylsuccinic anhydride use in SE1. The products were all glassy solid obtained in quantitative yield. The identity of the products was confirmed by C$^{13}$ and H$^1$ NMR. The products of these Examples were:

SE2—Octenyl succinic acid bis(N-methyl glucamide)
SE3—Decenyl succinic acid bis(N-methyl glucamide)
SE4—Tetradecenyl succinic acid bis(N-methyl glucamide)
SE5—Hexadecenyl succinic acid bis(N-methyl glucamide)
SE6—Octadecenyl succinic acid bis(N-methyl glucamide)
SE7—Dodecenyl succinic acid bis(N-methyl glucamide)

N-methyl glucamine (62.5 g; 0.32 mol) was added to a freshly prepared solution of dodecenyl acid dimethyl ester (50 g; 0.16 mol) (made as described in SE1) in polyethylene glycol 200 (PEG 200) (50 g). The reaction mixture was heated to 80° C. under vacuum, held at that temperature for 1 hour, then the temperature was raised to 100° C. and the reaction mix held at that temperature until no further methanol was evolved (about 8 hours). The product was obtained as a waxy solid in quantitative yield (including the PEG reaction solvenvdiluent). H$^1$ and C$^{13}$ NMR confirmed the identity of the product as the title compound.

SE8–SE11 Decenyl to Octadecenyl succinic acid bis(N-methyl glucamide)

The title compounds were made as described in Synthesis Example SE7, but substituting the corresponding alkenyl succinic acid dimethyl ester (made as described in SE2) for the dodecenyl succinic acid dimethyl ester used in SE7. The products was obtained as waxy solids in quantitative yield (including the PEG reaction solvent/diluent) and the identity of the products was confirmed by $C^{13}$ and $H^1$ NMR. The products of these Examples were:

SE8—Decenyl succinic acid bis(N-methyl glucamide)

SE9—Tetradecenyl succinic acid bis(N-methyl glucamide)

SE10—Hexadecenyl succinic acid bis(N-methyl glucamide)

SE11—Octadecenyl succinic acid bis(N-methyl glucamide)

SE12—Dodecenyl succinic acid bis(N-methyl glucamide)

The title compound was made by the method described in Synthesis Example SE7 except that monopropylene glycol (MPG) (50 g) was used as the solvent/diluent and the temperature of the reaction mixture was raised directly to 100° C. and maintained until methanol evolution ceased (about 8 hours). The product was obtained as a waxy solid in quantitative yield (including the MPG reaction solvent/diluent). The identity of the product was confirmed by $C^{13}$ and $H^1$ NMR.

SE13—Octadecenyl succinic acid N-methyl glucamide PEG 200 ester Octadecenyl succinic acid mono-PEG 200 ester PEG 200 (218.7 g; 1.09 mol) was added in a single portion to stirred octadecenyl succinic anhydride (382.8 g; 1.09 mol). The reaction mixture was heated to 100° C. for 2 hours after which the infra-red spectrum of a sample of the reaction mixture showed no sign of anhydride (stretch frequency 1790 cm$^{-1}$). A catalytic amount of sulphuric acid and methanol (50 ml) were added to the reaction mixture, the mixture heated to 110° C. and methanol/water mixture distilled out of the reaction. Fresh methanol was added at a rate to keep the reaction mixture volume constant. The end point of the reaction was determined from the infra-red and NMR spectra of samples. After completion of the esterification reaction, excess methanol was removed by distillation, the reaction mixture cooled, neutralisea and solids removed by filtration as described in SE1. The di-ester intermediate was obtained as a liquid in substantially quantitative yield and was used without further purification.

Octadecenyl succinnic acid N-methyl glucamide PEG 200 ester

N-methyl glucamine (67 g; 0.344 mol) was added in a single aliquot to octadecenyl succinic acid PEG 200 methyl ester (200 g; 0.334 mol) and the reaction mixture heated to 100° C. under vacuum until no more methanol was evolved (about 4 hours), when the $H^1$ NMR spectrum of a sample showed the absence of methyl ester. The title compound product was obtained as a waxy solid in substantially quantitative yield. The identity of the product was confirmed by $C^{13}$ and $H^1$ NMR.

SE14—SE18 Various alkenyl succinic N-methyl glucamide PEG esters

The title compounds were made as described in Synthesis Example SE13, but substituting the corresponding alkenyl succinic anhydride for the octadecenyl succinic anhydride and the corresponding PEG for the PEG 200 used in used in SE13. The products was obtained as waxy solids in quantitative yield and the identity of the products was confirmed by $C^{13}$ and $H^1$ NMR.

The products of these Examples were:

SE14—Dodecenyl succinic acid N-methyl glucamide PEG 600 ester

SE15—Dodecenyl succinic acid N-methyl glucamide PEG 2000 ester

SE16—Tetradecenyl succinic acid N-methyl glucamide PEG 600 ester

SE17—Octadecenyl succinic acid N-methyl glucamide PEG 1000 ester

SE18—Tetradecenyl succinic acid N-methyl glucamide methoxy PEG 180 ester

SE19—Bis|tetracenyl succinnic acid N-methyl glucamine| PEG 800 ester

The title compound was made by the general method of Example SE13, but using a 2:1 molar ratio of ASA:PEG to form the intermediate bis|tetradecenyl succinnic acid| PEG 800 ester; about twice the quantity of methanol (on a molar basis) to form the intermediate bis[tetradecenyl succinnic acid methyl ester] PEG 800 ester; and a 2:1 molar ratio of N-methylglucamine: bis(tetradecenyl succinnic acid methyl ester] PEG 800 ester. The product was obtained as a waxy solid in substantively quantitative yield. The identity of the product was confirmed by $C^{13}$ and $H^1$ NMR.

SE20—Hexadecenyl succinic acid bis-(N-diglucamide)

The title compound was made by the general method of Example SE12 but substituting diglucamine for the gulcamine and hexadecenyl acid dimethyl ester for the dodecenyl acid dimethyl ester used in Example SE12. The product was obtained as a waxy solid in substantively quantitative yield. The identity of the product was confirmed by $C^{13}$ and $H^1$ NMR.

SE21—Dodecenyl succinic acid N-methylglucamide N-di(2-ethylhexyl)amide Dodecenylsuccinic acid N-ethylhexylamide Di(2-ethylhexyl)amine (48.2 g; 0.2 mol) was added to dodecenyl succinic anhydride (53.2 g; 0.2 mol) over 2 to 3 minutes, the reaction mixture was heated to about 85° C. and stirred at this temperature for about 2 hours before being left to stir overnight at ambient temperature. The IR spectrum of a sample of the reaction mix showed no anhydride was present and had strong amide and carboxylic acid peaks. The reaction mix was used without further purification.

Dodecenyl succinic acid N-(2-ethylhexyl)amide methyl ester

The title compound was prepared as described in Example SE13 for making octadecenyl succinnic acid PEG 200 ester methyl ester, but using the dodecenyl succinic acid N-(2-ethylhexyl)amide from the preylous stage instead of the octadecenyl succinnic acid PEG 200 ester used in SE13. The title compound was obtained as a liquid in substantively quantitative yield. The structure of the compound was confirmed by $H^1$ and $C^{13}$ NMR spectra.

Dodecenyl succinic acid N-methylglucamide N-ethylhexylamide

The title compound was prepared as described in Example SE13 for making octadecenyl succinnic acid N-methylglucamide PEG 200 ester from the methyl ester precursor, but using dodecenylsuccinic acid N-(2-ethylhexyl)amide methyl ester from the previous stage instead of the octadecenyl succinnic acid PEG 200 ester methyl ester used in SE13. The title compound was obtained as a waxy solid in substantively quantitative yield. The structure of the compound was confirmed by $H^1$ and $C^{13}$ NMR spectra.

The properties of products made in the Synthesis Examples are summarised out in Table 1 below.

TABLE 1

| Example No | ST (mN.m$^{-1}$) | CP (°C.) | Wtg (s) | FH (mm) 0 min | FH (mm) 5 min |
|---|---|---|---|---|---|
| SE1 | 39.9 | >98 | 68 | 99 | 81 |
| SE2 | | | | | 33 |
| SE3 | 36.4 | >98 | 108 | 121 | 112 |
| SE4 | 37.3 | ambient | 237 | 36 | 33 |
| SE5 | 40.6 | >98 | >300 | 44 | 39 |
| SE6 | 55.1 | ambient | >300 | 13 | 11 |
| SE7 | | >98 | 106 | 107 | 96 |
| SE8 | 35.6 | >98 | >300 | 120 | 95 |
| SE9 | | >98 | 275 | 107 | 95 |
| SE10 | | >98 | >300 | 50 | 45 |
| SE11 | | ambient | >300 | 7 | 6 |
| SE12 | | >98 | | | |
| SE14 | | >98 | >300 | 20 | 18 |
| SE19 | | >98 | 126 | | |

Applications Examples AE1 to AE3 Agrochemical Formulation Applications

Application test methods

Weed control was assessed by generating European Weed Research Council (EWRC) ratings: where 1=no control and 9=100% control, at 3, 7, 14 and 28 days after treatment.

Inhibition Diameter (ID %)

the test is carried out by infecting a petri dish containing a suitable growth medium with the target fungus, once the fungus covers the surface of the medium, a small filter paper disc impregnated with the test formulation is placed on the surface of the disc, the area of the surface of the medium that becomes free of fungus is measured and the equivalent diameter is the ID. All ID values, used in subsequent calculations are the mean values of four replications. The larger the ID the better the result. Results are quoted as the numerical percentage of the ID for a test formulation based on the ID for the antifungal material applied at its normal application rate (NAR) without an adjuvant—the higher the percentage the more effective is the adjuvant). The test formulations are applied at half the normal application rate.

Fungal Growth Diameter (FGD %)

the test is carried out by making up a growth medium including a fungicide formulation and placing a disc infected with the target fungus onto the medium in a petri dish. The effectiveness of the formulation is measured by the area that becomes infected with the fungus. The larger the infected area the less effective is the formulation. Again all results are based on four replications of all runs. The area infected is expressed as an equivalent diameter and the results are quoted as an efficacy ratio (%) which is=100×(the diameter when no fungicide used—the diameter when the formulation contains fungicide)/(the diameter when no fungicide used).

Example AE1—Herbicide formulations containing Glyphosate

Herbicide formulations F1 to F8 based on glyphosate isopropylamine salt were made up by dissolying the glyphosate salt at 360 g.l$^{-1}$ and adjuvant (in some cases including a solvent or cosolvent) at 180 g.l$^{-1}$ in water. A control formulation CF1 was made up using ETA as the adjuvant (to give a typical current formulation for glyphosate herbicide). The formulations were used in a test spraying programme in which the formulation was sprayed onto test plots at a rate of 4Lha$^{-1}$ of formulation in a spray volume of 250 Lha$^{-1}$ using 4 replications. The formulations used and the weed control results obtained are summarised in Table 2 below.

TABLE 2

| Form No | Adjuvant material | (g.l$^{-1}$) | Cosolvent material | (g.l$^{-1}$) | Weed Control (EWDC) at (days) 3 | 7 | 14 | 28 |
|---|---|---|---|---|---|---|---|---|
| CF1 | ETA | 180 | — | | 2 | 4.5 | 7 | 9 |
| F1 | SE 2 | 180 | — | | 3 | 5.5 | 7 | 9 |
| F2 | SE 3 | 90 | MPG | 90 | 4 | 6 | 8 | 9 |
| F3 | SE 2 | 90 | MPG | 90 | 4 | 6 | 7.5 | 9 |
| F4 | SE 1 | 90 | MPG | 90 | 3.5 | 6 | 7.5 | 9 |
| F5 | SE 2 | 90 | water | 90 | 3.5 | 5 | 7 | 9 |
| F6 | SE 3 | 180 | — | | 3 | 6 | 7 | 9 |
| F7 | SE 1 | 180 | — | | 3 | 5 | 7.5 | 9 |

Example AE2—Herbicide formulations containing Sulfosate

Herbicide formulations F9 to F16 based on glyphosate as the trimethyl sulphonium salt were made up by dissolying the sulfosate at 360 g.l$^{-1}$ and adjuvant (in some cases including a solvent or cosolvent) at 180 g.l$^{-1}$ in water. A control formulation CF2 was made up using AL 2042 as the adjuvant (to give a typical current formulation for sulphosate herbicide). The formulations were used in a test spraying programme in which the formulation was sprayed onto test plots at a rate of 3 l.ha$^{-1}$ of formulation in a spray volume of 250 l.ha$^{-1}$ using 4 replications. The formulations used and the weed control results obtained are summarised in Table 3 below.

TABLE 3

| Form No | Adjuvant material | (g.l$^{-1}$) | Cosolvent material | (g.l$^{-1}$) | Weed Control (EWDC) at (days) 3 | 7 | 14 | 28 |
|---|---|---|---|---|---|---|---|---|
| CF2 | AL 2042 | 360 | — | | 4 | 7 | 8 | 9 |
| F8 | SE 2 | 360 | — | | 4 | 6.5 | 8 | 9 |
| F9 | SE 3 | 180 | MPG | 180 | 4 | 6 | 7 | 9 |
| F10 | SE 2 | 180 | MPG | 180 | 4 | 6.5 | 8.5 | 9 |
| F11 | SE 1 | 180 | MPG | 180 | 4 | 6 | 8 | 9 |
| F12 | SE 2 | 180 | water | 180 | 4 | 7 | 8 | 9 |
| F13 | SE 3 | 360 | — | | 4 | 6.5 | 8 | 9 |
| F14 | SE 1 | 360 | — | | 4 | 6.5 | 8 | 9 |

Example AE3—Antifungal formulations

Various antifungal formulations were made up and tested in vitro by the methods described above. The antifungal materials used were conventional commercially available materials. The effectiveness of the surfactants of this invention as adjuvants was assessed by making up appropriate formulations, testing them and comparing them with formulations not using the adjuvants. The formulations and results are summarised in Table 4 below in which the adjuvants are identified by their Synthesis Example (SE) numbers.

TABLE 4

| commercial formulation active constituent: | Calixin Trimedorf | Rovral Ipridone | Carben VL Carbendazim | Tilt Propiconazole |
|---|---|---|---|---|
| concentration: | 250 g.l$^{-1}$ EC | 500 g.l$^{-1}$ SC | 500 g.l$^{-1}$ SC | 250 g.l$^{-1}$ EC |
| fungus | Fusanum Sambucinum | Botrytis Cinerea | Septoria Apiicola | Septoria Apiicola |
| NAR | 0.3% | 0.1% | 0.1% | 0.1% |
| adjuvant | | Test Results | | |
| concn. (%) | ID (%) | ID (%) | FDG (%) | FDG (%) |
| Control 0 | 68.1 | 71.8 | 20.4 | 38.9 |
| SE1 0.05 | 70.2 | 97.1 | 41.6 | 70.5 |
| 0.1 | 78.7 | 106.2 | 57.9 | 73.8 |
| 0.2 | 92.3 | 115.5 | 65.9 | 77.3 |
| SE2 0.05 | 68.1 | 80.8 | 20.4 | 63.6 |
| 0.1 | 74.5 | 87.3 | 32.9 | 68.0 |
| 0.2 | 76.6 | 108.7 | 44.3 | 70.5 |
| SE4 0.05 | 72.3 | 78.0 | 41.6 | 72.7 |
| 0.1 | 78.7 | 94.4 | 52.9 | 76.2 |
| 0.2 | 96.6 | 103.4 | 64.8 | 78.4 |
| SE5 0.05 | 76.6 | 89.3 | 50.0 | 77.3 |
| 0.1 | 85.1 | 109.0 | 62.0 | 79.5 |
| 0.2 | 92.3 | 118.9 | 68.2 | 81.8 |
| SE6 0.05 | 74.5 | 80.3 | 35.2 | 69.3 |
| 0.1 | 80.8 | 89.3 | 42.0 | 71.5 |
| 0.2 | 93.6 | 102.3 | 50.6 | 72.7 |

Applications Examples AE4 Pigment Dispersion

Dispersions of pigment grade TiO$_2$ in water were made up based on the following formulation:

| Material | wt. (g) |
|---|---|
| TiO$_2$ pigment | 65 |
| Surfactant | 1 |
| n-hexanol - anti-foam | 0.5 |
| water | to 100 |

The surfactant was weighed in a 250 ml glass bottle. the calculated amount of demineralised water was added followed by the n-hexanol and the mixture was mixed gently to bring the surfactant into solution . 3 mm glass beads (about 50 g) were added followed by the pigment. The dispersion was agitated using a Red Devil laboratory shaker for ½ hour. The viscosity of the dispersion was measured using a Brookfield LVT viscometer at 6 rpm (0.1 Hz). The viscosity of the dispersion and the surfactants used are reported in Table 5 below.

TABLE 5

| Run No | Surfactant (SE No) | Viscosity (mPa.s) |
|---|---|---|
| 1 | 1 | 12 |
| 2 | 4 | 13 |
| 3 | 5 | 12 |
| 4 | 6 | 11 |

Applications Examples AE5 Domestic Detergency—Laundry Liquids

Test formulations of a heavy duty non-aqueous laundry liquid were made up as follows:

| Material | pts by wt |
|---|---|
| sodium disilicate | 2.0 |
| optical brightener | 0.3 |
| EDTA | 0.2 |
| carboxy methyl cellulose | 1.0 |
| TiO$_2$ pigment | 0.2 |
| Sodium Carbonate | 4.9 |
| Sodium tri-polyphosphate | 40.9 |
| PEG 200 | 39.4 |
| Product of SE1 | 10.0 |

The formulations were tested by use in a Tergotometer washing machine (made by the United States Testing Company) with water of standard hardness 50 or 300 ppm at 40° or 60° C. and using 3 g.I$^{-1}$ or 6 g.I$^{-1}$ of formulation (a total of eight runs). Each wash used four standard test soiled cloths viz: EMPA polycotton 101, EMPA polycotton 104, Krefeld cotton 10C, Krefeld polycotton 20C. The reflectance of the cloths was measured before and after washing and the percentage increase in reflectance is reported as the test result. The results are set out in Table 6 below.

TABLE 6

| Run No | Hard. (ppm) | Temp. (°C.) | Conc$^n$ (g.l$^{-1}$) | Increase in Reflectance on washing (%) | | | |
|---|---|---|---|---|---|---|---|
| | | | | EMPA 101 | EMPA 104 | Krefeld 10C | Krefeld 20C |
| 1 | 300 | 40 | 3 | 24.5 | 45 | 26.9 | 40.8 |
| 2 | 50 | 40 | 3 | 34 | 47.8 | 36.7 | 47.6 |
| 3 | 300 | 40 | 6 | 32.2 | 46.8 | 35.7 | 50.1 |
| 4 | 50 | 40 | 6 | 34.8 | 48.1 | 37 | 51.2 |
| 5 | 300 | 60 | 3 | 43.7 | 49.4 | 44.4 | 47.9 |
| 6 | 50 | 60 | 3 | 46.8 | 48.6 | 46.1 | 51 |
| 7 | 300 | 60 | 6 | 48.7 | 49.2 | 47.1 | 51.9 |
| 8 | 50 | 60 | 6 | 48.8 | 49.1 | 46.7 | 52.7 |

We claim:

1. A succinic acid derivitve of the formula (I):

where
one of $R^1$ and $R^2$ in the succinic acid derivitve is $C_6$ to $C_{22}$ alkenyl or alkyl and the other is hydrogen;
$R^3$ is a polyhydroxy hydrocarbyl radical;
$R^4$ is hydrogen, $C_1$ to $C_{22}$ hydrocarbyl, or $R^4$ is independently as defined above for $R^3$;

$R^5$ is a group: —$NR^3R^4$ where $R^3$ and $R^4$ are independently as defined above; or $R^5$ is a group: —$O.(AO)_n.R^6$ where:
AO is an alkylene oxide residue;
n is 1 to 200; and
$R^6$ is hydrogen or $C_1$ to $C_{22}$ hydrocarbyl; or
$R^6$ is a group:

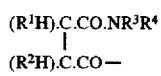

where $R^1$, $R^2$, $R^3$ and $R^4$ are independently as defined above; or $R^6$ is a group: —$NR^7R^8$ where:
$R^7$ is hydrogen or $C_1$ to $C_{22}$ hydrocarbyl; and $R^8$ is $C_1$ to $C_{22}$ hydrocarbyl; or
—$NR^7R^8$ is a pyrrolidino-, piperidino-, morpholino-, piperazino, or a N—($C_1$ to $C_6$ alkyl) piperazino- group; or
—$NR^7R^8$ is a group of the formula —$NH.(AO)_n.R^9$ where AO and n are as defined above and $R^9$ is a $C_1$ to $C_{22}$ hydrocarbyl group; or
—$NR^7R^8$ is a group of the formula —$NH.(AO)_p.CH_2CH_2.OR^{10}$
where AO is as defined above; p is from 0 to 200; and $R^{10}$ is a $C_1$ to $C_{22}$ hydrocarbyl; or
$R^{10}$ is a group:

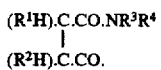

where $R^1$, $R^2$, $R^3$ and $R^4$ are independently as defined above.

2. A compound as claimed in claim 1 having the formula (Ia):

where $R^1$, $R^2$, $R^3$ and $R^4$ are independently as defined in claim 1.

3. A compound as claimed in claim 1 having the formula (Ib):

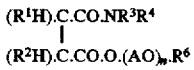

where $R^1$, $R^2$, $R^3$, $R^4$, AO, n and $R^6$ are as defined in claim 1.

4. A compound as claimed in claim 1 having the formula (Ic):

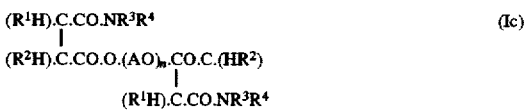

where $R^1$, $R^2$, $NR^3R^4$, AO and n are as defined in claim 1.

5. A compound as claimed in claim 1 having the formula (Id):

where $R^1$, $R^2$, $R^3$, $R^4$, AO, n and $R^9$ are as defined in claim 1.

6. A compound as claimed in claim 1 having the formula (Ie):

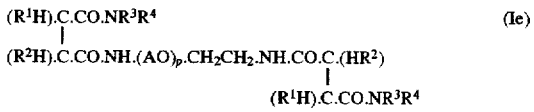

where $R^1$, $R^2$, $R^3$, $R^4$, AO and p are as defined in claim 1.

7. A compound as claimed in claim 1 having the formula (If):

where $R^1$, $R^2$, $R^3$, $R^4$, $R^7$ and $R^8$ are as defined in claim 1.

8. A compound as claimed in claim 1 wherein one of $R^1$ and $R^2$ in the succinic acid moiety is a $C_8$ to $C_{18}$ straight chain alkenyl group and the other is hydrogen.

9. A compound as claimed in claim 1 wherein $R^3$ is of the formula:
—$CH_2.(CHOH)_4.CH_2OH$ and $R^4$ is hydrogen, or a methyl, ethyl, propyl or butyl group.

10. A compound as claimed in claim 1 wherein $R^4$ is a $C_1$ to $C_{20}$ alkyl, $C_7$ to $C_{12}$ aralkyl or $C_2$ to $C_{20}$ hydroxyl substituted alkyl group; AO is an ethylene oxide residue; n and p are each independently from 3 to 50; $R^6$, $R^7$, $R^8$ and $R^{10}$ are each independently a $C_1$ to $C_6$ alkyl group; and $R^9$ is a $C_1$ to $C_{22}$ alkyl group.

11. A compound as claimed in claim 1 wherein there are plural groups $R^1/R^2$ and/or —$NR^3R^4$ and the respective groups $R^1/R^2$ and —$NR^3R^4$ are the same.

12. A method of making a compound as claimed in claim 1 which comprises reacting an ester of a corresponding substituted succinic acid with an alcohol of the formula $R^{11}OH$, where $R^{11}$ is a $C_1$ to $C_4$ alkyl group, with an amine of the formula $H.NR^3R^4$, where $R^3$ and $R^4$ are as defined in claim 1, in a molar ratio corresponding to the number of —$NR^3R^4$ amide functions in the final product and removing the alcohol $R^{11}OH$ generated by distillation.

13. An agrochemical formulation which includes at least one agrochemically active component and a compound as claimed in claim 1 as a surfactant and/or adjuvant.

14. An agrochemical formulation as claimed in claim 13 including one or more herbicides such as glyphosate and sulfosate, fungicides such as Iprodione, Carbendazym and Propionazole, insecticides, acaricides and/or plant growth regulators as agrochemically active component(s).

15. An agrochemical formulation as claimed in claim 13 further including one or more oils; solvents and/or diluents; and other anionic, cationic, or non-ionic surfactants.

16. A dispersion of a pigment in a liquid carrier including as a dispersant a compound of the formula (I) as defined in claim 1.

17. A dispersion as claimed in claim 16 wherein the pigment is titanium dioxide and the liquid carrier is water.

18. A dispersion as claimed in claim 16 wherein the compound of the formula (I) is used in an amount of 0.2 to 10% by weight of the pigment.

19. A paint including a dispersion of a pigment as claimed in claim 16.

20. A domestic detergent which includes at least one compounds as claimed in claim 1 as surfactants.

21. A domestic detergent in the form of a non-aqueous heavy duty laundry liquid which includes at least one compound as claimed in claim 1 as surfactants.

22. A domestic detergent as claimed in claim 20 which further includes one or more of other, non-ionic, anionic and/or cationic surfactants; builders; corrosion inhibitors; anti-redeposition aids such as carboxy methyl cellulose; optical brighteners; perfumes; one or more lipase, protease, cellulase and/or amylase enzymes; bleaches optionally with one or more bleach activators and/or stabilisers: soaps; foam control agents; and fabric conditioners.

* * * * *